United States Patent [19]
Feler et al.

[11] Patent Number: 6,027,456
[45] Date of Patent: Feb. 22, 2000

[54] APPARATUS AND METHOD FOR POSITIONING SPINAL CORD STIMULATION LEADS

[75] Inventors: Claudio A. Feler, Memphis, Tenn.; John H. Erickson, Plano; Steven P. Rhines, McKinney, both of Tex.

[73] Assignee: Advanced Neuromodulation Systems, Inc., Allen, Tex.

[21] Appl. No.: 09/113,390

[22] Filed: Jul. 10, 1998

[51] Int. Cl.[7] .................................................. A61B 5/05
[52] U.S. Cl. .......................................... 600/554; 607/117
[58] Field of Search .................................. 600/554, 643; 607/863, 117

[56] References Cited

U.S. PATENT DOCUMENTS

| | | | |
|---|---|---|---|
| 4,570,640 | 2/1986 | Barsa | 128/741 |
| 5,081,999 | 1/1992 | Deletis | 128/642 |
| 5,313,956 | 5/1994 | Knutsson et al. | 128/741 |
| 5,417,719 | 5/1995 | Hull et al. | 607/46 |
| 5,643,330 | 7/1997 | Holsheimer et al. | 607/46 |
| 5,687,724 | 11/1997 | Jewett et al. | 128/653.1 |

*Primary Examiner*—William E. Kamm
*Attorney, Agent, or Firm*—Sidley & Austin

[57] ABSTRACT

An apparatus for assisting in the placement of a spinal cord stimulation lead with respect to the dorsal column of a patient. The apparatus detects evoked potentials which result from the controlled stimulation of spinal nerves and provides information to an operator to allow a stimulation lead to be positioned relative to a physiological midline and/or positioned along the dorsal column in a longitudinal direction.

20 Claims, 4 Drawing Sheets

APPARATUS AND METHOD FOR POSITIONING SPINAL CORD STIMULATION LEADS

FIELD OF THE INVENTION

The present invention relates to a medical device to facilitate positioning of spinal cord stimulation leads, and in particular, to a medical device to enable the accurate placement of spinal cord stimulation leads without intraoperative, conscious patient feedback.

BACKGROUND OF THE INVENTION

Application of specific electrical fields to spinal nerve roots, spinal cord, and other nerve and bundles for the purpose of chronic pain control has been actively practiced since the 1960s. While a precise understanding of the interaction between the applied electrical energy and the nervous tissue is not fully appreciated, it is known that application of an electrical field to spinal nervous tissue (i.e., spinal nerve roots and spinal cord bundles) can effectively mask certain types of pain transmitted from regions of the body associated with the stimulated tissue. More specifically, applying particularized electrical pulses to the spinal cord associated with regions of the body afflicted with chronic pain can induce paresthesia, or a subjective sensation of numbness or tingling, in the afflicted bodily regions. This paresthesia can effectively mask the transmission of non-acute pain sensations to the brain.

It is known that each region of the human body is associated with a particular spinal nerve root. As shown in FIG. 1, the dermatomes of the human body are mapped, and each dermatome corresponds to a longitudinal spinal position. As can be seen, the head and neck regions are associated with C2–C8, the back is from C2–S3, the central diaphragm is between C3 and C5, the upper extremities are between C5 and T1, the thoracic wall is between T1 and T11, the peripheral diaphragm is between T6 and T11, the abdominal wall is associated with T6–L1, lower extremities are located from L2 to S2, and the perineum from L4 to S4. By example, to address chronic pain sensations which commonly focus on the lower back and lower extremities, a specific energy field can usually be applied to a region between bony level T8 and T10. As should be understood, successful pain management and the avoidance of stimulation in unafflicted regions necessarily requires the applied electric field to be properly positioned longitudinally along the dorsal column.

Positioning of an applied electrical field relative to a physiological midline is equally important. Nerve fibers extend between the brain and a nerve root along the same side of the dorsal column as the peripheral areas the fibers represent. Pain which is concentrated on only one side of the body is "unilateral" in nature. To address unilateral pain, electrical energy is applied to the related neural structures lying on the same side of the dorsal column as the afflicted region of the body. Pain which is present on both sides of a patient is "bilateral." Accordingly, bilateral pain is addressed through either an application of electrical energy along a patient's physiological midline or an application of electrical energy about each side of the physiological midline, where in the latter case the electric energy is caused to traverse the critical midline.

Pain managing electrical energy is commonly delivered through electrodes positioned external to the dural layer surrounding a spinal cord. The electrodes are carried by two primary vehicles: the percutaneous catheter and the laminotomy lead.

Percutaneous catheters, or percutaneous leads, commonly have two or more electrodes and are positioned above the dura layer through the use of a Touhy-like needle which passes through the skin, between the desired vertebrae, and opens above the dura layer. For unilateral pain, percutaneous leads are positioned on the afflicted side, as discussed above, and for bilateral pain, a single percutaneous lead is positioned along the patient midline or at least two leads are positioned on each side of the midline. Insertion and positioning of percutaneous leads are typically performed under a local anesthetic.

Laminotomy leads have a paddle configuration and typically possess a plurality of electrodes (for example, two, four, eight, or sixteen) arranged in independent columns. An example of an eight-electrode laminotomy lead is shown in FIG. 2. The illustrated laminotomy lead is a LAMITRODE® 44 lead manufactured by Advanced Neuromodulation Systems, Inc. of Allen, Tex.

Implanted laminotomy leads are commonly aligned with the physiological midline of a patient. In such position, multiple columns of electrodes are well suited to address both unilateral and bilateral pain, where electrical energy may be administered using either column independently (on either side of the midline) or administered using both columns to create an electric field which traverses the midline.

While the larger size and configuration of laminotomy leads provide increased stability once implanted, laminotomy leads require a surgical procedure for implantation. The surgical procedure, or partial laminectomy, requires the resection and removal of certain vertebral tissue to allow both access to the dura and proper positioning of a laminotomy lead. Unlike the insertion of percutaneous leads, this procedure can result in considerable discomfort for the patient. However, not unlike the use of percutaneous leads, the implanting physician must necessarily rely on patient feedback following trial stimulation to identify at least a proper medial/lateral position of the lead.

The implanting physician has the following alternatives when implanting laminotomy leads: (i) administer a local anesthetic and discuss the positioning of the lead(s) with the patient during an intraoperative trial; (ii) administer an epidural anesthetic and discuss the positioning of the lead(s) with the patient during an intraoperative trial; (iii) place the patient under a general anesthetic, and once the site of implantation is prepared, awaken the patient for an intraoperative trial; or (iv) place the patient under a general anesthetic and position the lead(s) in accordance with a determined anatomic midline of the patient. For (i), the patient is subjected to the greatest discomfort. Accordingly, the value of the feedback provided can be vitiated by the patient's desire to conclude the procedure quickly and inadvertently sacrifice optimization for short-term relief. For alternatives (ii) and (iii), the patient can experience impaired perceptions which can prevent the preferred placement of the lead(s). While alleviating the discomfort of the patient, alternative (iv) is susceptible to the common occasion when the anatomic and physiological midlines are not aligned, thereby preventing optimized medial placement of the lead(s).

Errors in initial lead placement can require additional corrective surgery. As should be appreciated, additional surgeries increase the discomfort of the patient as well as subject the patient and/or the health care system to additional cost burdens.

Consequently, a need exists for a device and method to enable an implanting physician to accurately and quickly position one or more spinal cord stimulating leads while minimizing the operative a discomfort of the patient.

SUMMARY OF THE INVENTION

The present invention is directed to a spinal cord stimulation lead positioning apparatus. The apparatus enables the positioning of percutaneous and laminotomy leads within a patient under a general anesthetic. The apparatus includes a signal generating device for generating a stimulation signal, where the stimulation signal is delivered to the spinal nerves of the patient via at least two stimulation electrodes of each lead to be implanted. The apparatus further includes at least two detection electrodes adapted to be positioned at or about the head of the patient to detect a bodily reaction to a stimulation signal from the signal generating device, and a feedback device, coupled to the at least two detection electrodes, to display information corresponding to a medial/lateral position of the at least two stimulation electrodes relative to a physiological midline of the patient.

In another embodiment of the present invention, one or more additional detection electrodes are provided which are positioned about the body of the patient to detect a bodily reaction to the stimulation signal from the signal generating device, wherein a position of each additional detection electrode corresponds to a bodily region subject to manageable pain. The additional detection electrodes are also coupled to the feedback device which further displays information corresponding to a longitudinal position of the at least two stimulation electrodes with respect to the dorsal column of the patient.

An object of the present invention is to overcome the known limitations for the implantation of spinal cord stimulation leads so as to ensure the proper positioning of the leads and provide optimized stimulation.

Another object of the present invention is to enable the implantation of one or more spinal cord stimulation leads without conscious patient feedback.

Another object of the present invention is to provide clear, interpretable information to a physician during a spinal cord stimulation lead implantation procedure to empower at least the medial/lateral placement of one or more leads at a given vertebral position of the patient.

Other objects and advantages of the present invention will be apparent to those of ordinary skill in the art having reference to the following Specification together with the drawings.

BRIEF DESCRIPTION OF THE DRAWINGS

Referring now to the drawings in which like reference numerals and letters indicate corresponding elements throughout the several view, if applicable.

DETAILED DESCRIPTION OF THE PREFERRED EMBODIMENTS

For simplification, the human nervous system includes two primary parts: the central nervous system and the peripheral nervous systems. The central nervous system includes the brain and the spinal cord, while the peripheral nervous system includes cranial and spinal nerves and their associated nerve ganglia, autonomic nerves and their associated nerve ganglia, and neuro receptors and effectors.

Figure 1:
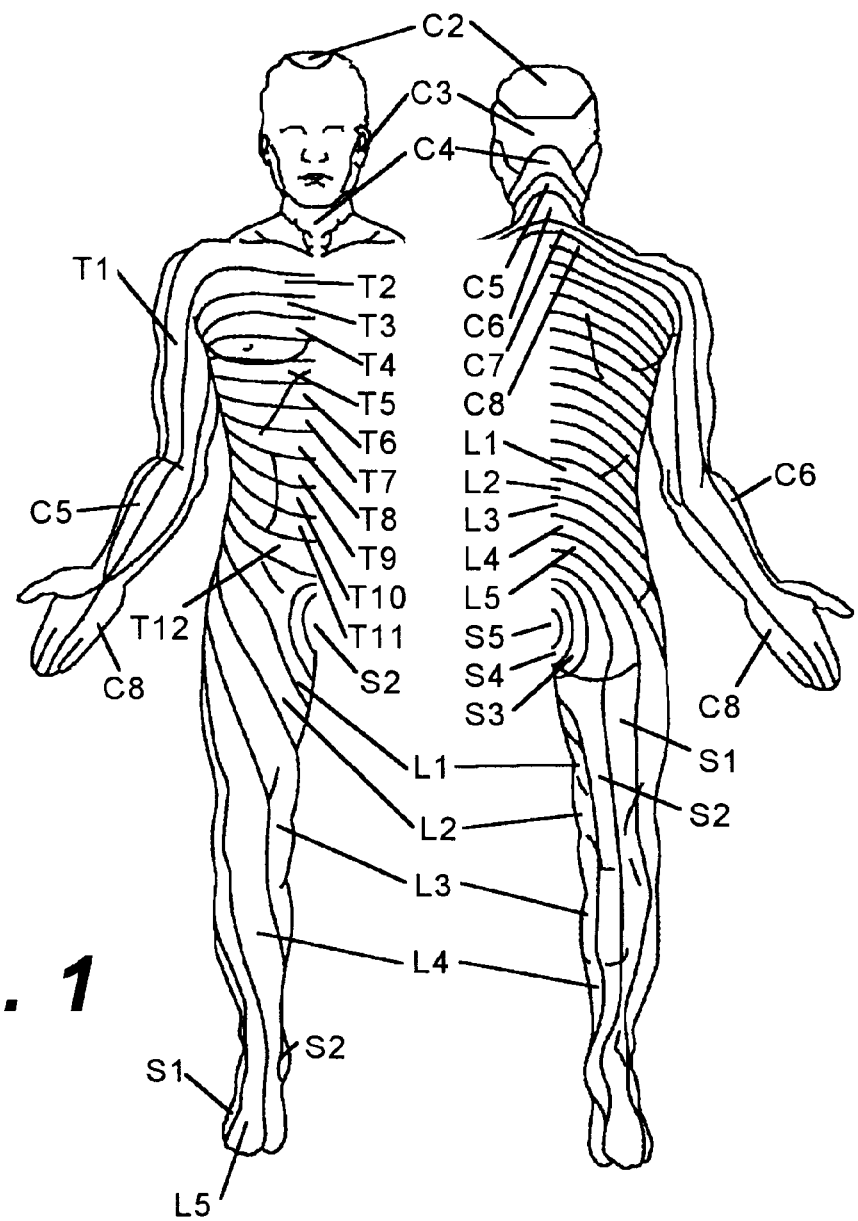
FIG. 1 is a dermatome map of the human body.
Figure 2:
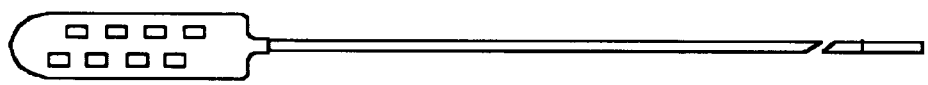
FIG. 2 is a conventional laminotomy spinal cord stimulation lead.

The nervous system receives sensory inputs through a somatic sensory division and an autonomic input division and outputs responses through a somatic motor division and an autonomic output division. In particular, spinal nerves transmit the inputs and outputs of the nervous system, as the spinal nerves extend from the spinal cord out to the muscles and overlying skin of the body and its extremities. The vertebral position from which each spinal nerve departs the vertebral column is indicative of a specific dermatome relationship (see FIG. 1) and is further used to classify the differing nerve roots, for example, cervical, thoracic, lumbar, sacral, and coccygeal.

The somatic sensory system transmits sensory information from the regions of the body to the central nervous system using the network discussed above. The somatic sensory system is sensitive to and transmits information concerning mechanical sensations (e.g., displacement, pressure, touch, muscle tension), thermal sensations, and pain. Specifically, the somatic sensory system receives a stimulus and coverts it to a specific electric current and sends the current to the central nervous system along a largely direct path. Once the individual currents are received within the cerebral cortex, they are appropriately acted upon, whether stored in memory or the subject of a responsive motor action.

Due to its consistent, systematic response, the somatic sensory system may be evaluated to detect input and/or output interruptions along nerve pathways in the central nervous system or between the central nervous system and a peripheral nervous system. An example of somatic sensory system assessment could involve application of electrical stimulation to a human extremity (e.g., a foot) and measuring the lapsed time necessary to detect evoked electroencephalographic (EEG) activity. While detection electrodes may be positioned elsewhere (for example, along the spinal column), placement at or about the head of the patient assists in reducing noise interference associated with cardiac activity and other muscle activity.

For an average adult male, the lapsed time between application of a prescribed electrical pulse to a foot and detection of an evoked response within the cerebral cortex is approximately 39 ms. Failure to detect responsive cerebral activity or lapses of time significantly greater than statistical averages can be indicative of nerve pathway interruptions—damage following injury or intentional nerve blocks associated with applied anesthetic during a medical procedure or as a treatment for chronic pain.

Figure 3:
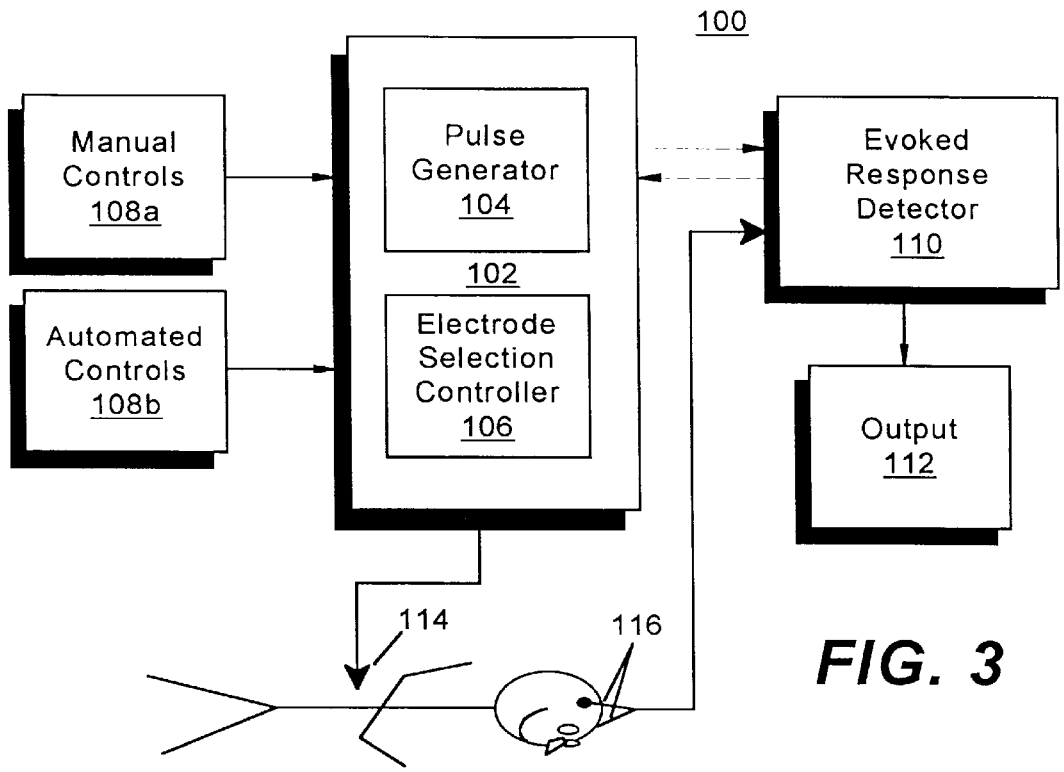
FIG. 3 illustrates a spinal cord placement apparatus in accordance with the present invention.

FIG. 3 illustrates a first embodiment of the spinal cord stimulation lead placement device 100 of the present invention. This embodiment of device 100 enables at least the medial/lateral positioning of stimulation leads(s) 114 with respect to a physiological midline of a patient. Device 100 includes, in part, stimulation controller 102 having pulse generator 104 and electrode selection controller 106. Controller 102 is responsive to input controls 108a and 108b, discussed below.

Pulse generator 104 is preferably conventional and has an operational range consistent with conventional spinal cord stimulation devices. For example, a conventional spinal cord stimulation device can generate an electrical stimulation pulse having an amplitude of 0–12 V, a frequency of 10–1,500 Hz, a pulse width of 50–500 $\mu s$, and a definable pulse polarity.

Responsive to input controls 108a and 108b for directing the generated pulse of pulse generator 104, electrode selection controller 106 effects selection of at least one positively biased electrode and at least one negatively biased electrode from spinal stimulation lead(s) 114 to enable the formation of an electric field. Stimulation lead(s) 114 preferably include a plurality of electrodes. The number of electrodes directly corresponds to the number of possible electrode combinations which may be used to generate one or more electric fields. Importantly, differing electric fields applied to a particular nerve group can effect a variety of results. Accordingly, controller 106 can facilitate assessments of stimulation lead 114 placement by allowing the selective activation and control of each of the plurality of electrodes of the stimulation lead(s) 114.

Input controls 108a and 108b include manual controls 108a and automated controls 108b. Manual controls 108a allow a user to select and individually control the electrodes of stimulation lead(s) 114 as well as the characteristics and duration of an applied stimulation pulse. In contrast, automated controls 108b is a programmable controller which, when initiated, causes a stimulation pulse of a prescribed duration to be delivered via a predefined plurality of electrodes of stimulation lead(s) 114. The stimulation programs for automated controls 108b may be used to assist in placement as well as determine the efficacy of placement. While input controls 108a and 108b may take the form of external controllers, computers, or programmable devices, input control 108a and/or input control 108b may also be integrally formed with controller 102.

While the above description is directed to an output portion of device 100, device 100 further includes a complementary detection portion. The detection portion includes evoked response detector 110 coupled between output device 112 and detection electrodes 116. Detection electrodes 116 are preferably conventional EEG electrodes which may be safely adhered to the head of a patient and are positioned to detect medial/lateral cerebral activity. While an accurate detection of cerebral activity is required, any number of detection electrodes 116 may be used to achieve this goal. For conventional EEG electrodes, it is preferable that a plurality of electrodes are positioned about the head of the patient, for example, at least four electrodes per cranial hemisphere.

Activity detected by electrodes 116 is passed to detector 110. Detector 110 may perform varying degrees of signal modification and/or abridgement. Specifically, detector 110 may generally allow an input signal to pass without significant alteration (FIG. 4) or, alternatively, detector 110 may simplify the observable output and consequently perform a greater degree of analysis and modification (FIG. 5).

Figure 4:
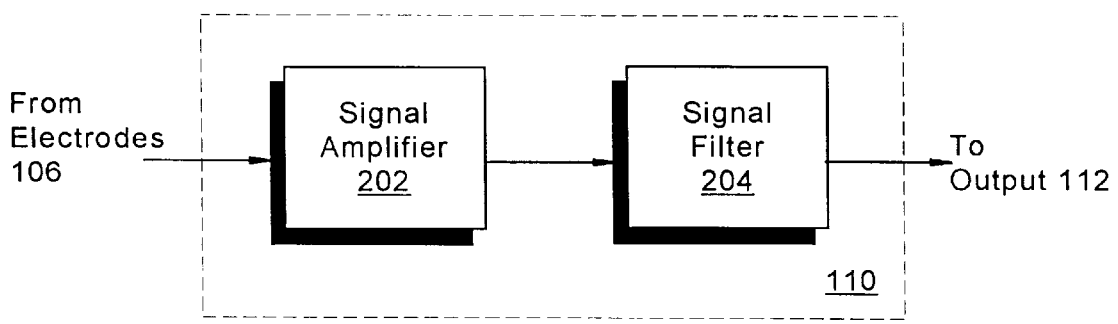
FIG. 4 illustrates one embodiment of an evoked potential detector of the apparatus of FIG. 3.

FIG. 4 illustrates a passive detector 110. Specifically, an input signal passes through certain threshold signal amplifiers 202 and noise filters 204 to prepare the signal for presentation. The filters serve to remove certain ambient activity, e.g., spontaneous activity of the cerebral cortex and muscle activity of the eyes, from the input signal. The processed signal is then passed to display device 112 for real-time presentation of detected evoked potentials.

When pulse generator 104 is inactive and the patient is under a general anesthetic, display 112 will show relatively inactive cerebral activity. As stimulation is applied through electrodes 114, display 112 will reflect evoked disturbances in the previously detected non-stimulated state. Consistent with the human anatomy, unilateral stimulation on the right side of the patient will produce a detected evoked response on the left side of the cerebral cortex. Likewise, unilateral stimulation on the left side of the patient will produce an evoked potential of the right side of the cerebral cortex. Medial placement of applied stimulation will result in substantially "balanced", or mutual, evoked responses from the left and the right sides of the cerebral cortex. Consequently, application of continuous or intermittent stimulation allows a user to readily assess medial/lateral positioning of one or more stimulation lead(s) 114 through evaluating the detected disturbances visually presented via display 112.

Figure 5:
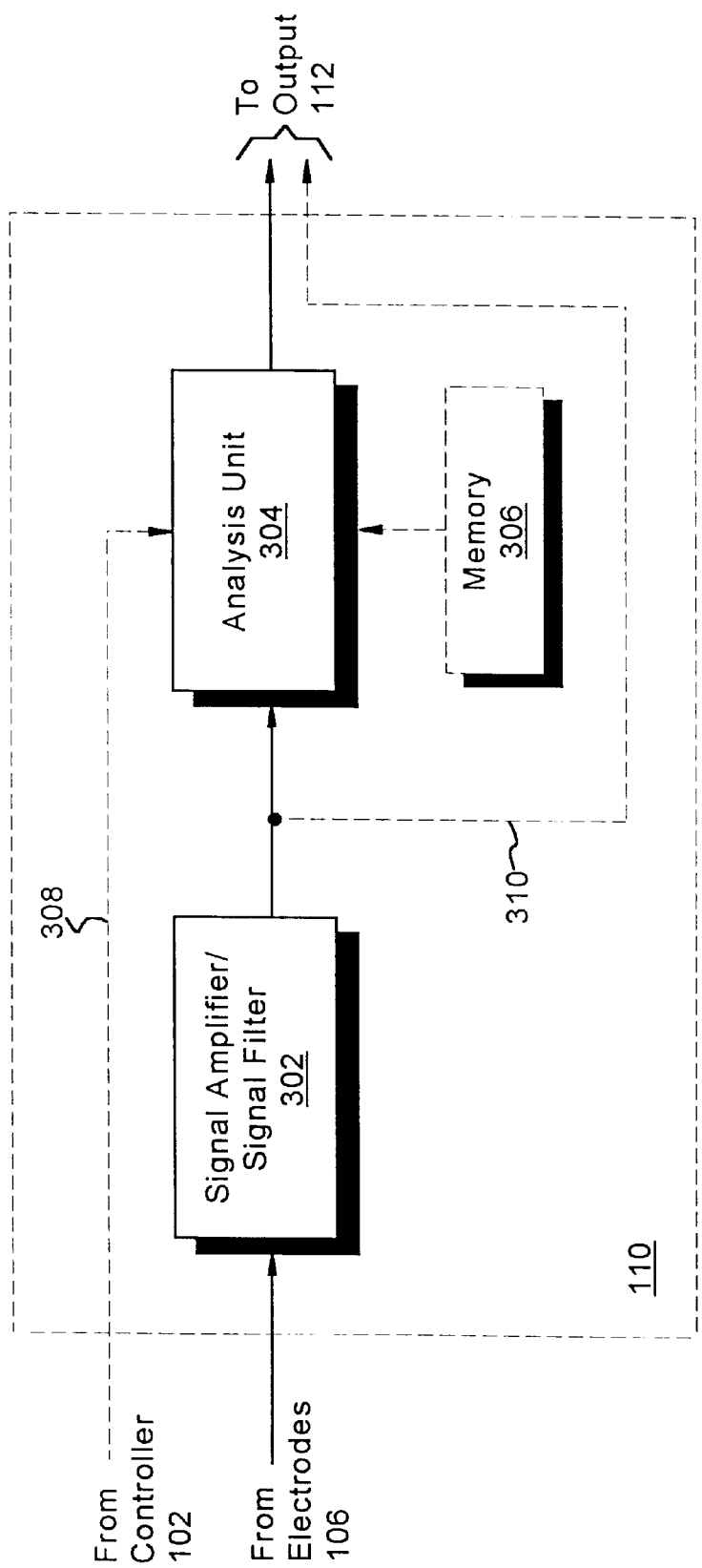
FIG. 5 illustrates another embodiment of an evoked potential detector of the apparatus of FIG. 3.
Figure 6:
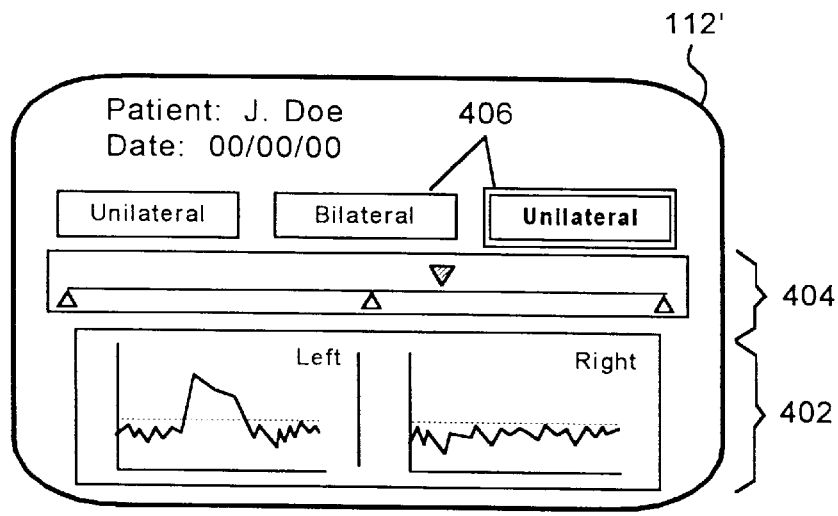
FIG. 6 illustrates a display output of the apparatus of FIG. 3.

FIG. 5 illustrates an active detector 110 which processes a signal input from electrodes 106 and is capable of outputting information requiring less analog interpretation. FIG. 6, for example, illustrates output display 112' which simply indicates medial and lateral positioning of stimulation lead (s) 114, the relative medial/lateral position of stimulation lead(s) 114 per a predefined scale, and/or include real-time information consistent with the output of detector 110 of FIG. 4.

Consistent with detector 110 of FIG. 4, input data from electrodes 106 is subjected to pre-analysis amplification and filtering in element 302 to remove a substantial portion of the ambient noise and the like. The signal is then passed to analysis unit 304. Analysis unit 304 may perform any variety of comparisons or analysis to output a signal, or signals, to output device 112.

In one embodiment, analysis unit 304 compares the magnitude of a detected evoked potential against data stored in memory 306. The stored data could include patient-specific information or statistically weighted information that establishes a baseline activity (i.e., non-stimulated, unconscious, background cerebral activity), where any detected evoked potential which exceeds the baseline is indicative of applied stimulation. The patient-specific information may be obtained at the time of the procedure or over the course of prior visits with the user, where a baseline may be established in a conventional manner.

In another embodiment, memory 306 may include patient-specific information or statistically weighted information concerning the lapsed time between stimulation and a corresponding evoked potential for a particular region of the body, for example, the heels, the hands, or other extremities. Analysis unit 304 will compare information from pulse generator 104 against the stored lapsed time data, or a correlation of this data, to exclude information from filter/ amplifier 302 which occurs outside of a supported time frame having a margin of error. For example, if the known time between stimulation and detection of a corresponding evoked potential is 20 ms, analysis unit 304 would exclude that data input from filter/amplifier 302 which did not fall within a 20±1 ms range, wherein the ±1 ms is a predetermined margin of error.

Analysis unit 304 is notified of application of a stimulation pulse over data input line 308 which couples analysis unit 304 and pulse generator 104. A notification signal from pulse generator 104 triggers a clock (not shown) within analysis unit 304. Accordingly, a measured lapsed time is subsequently compared to that information extracted from memory 306.

Analysis unit 304 may require specific time lapse data (i.e., from implantation point to head) for above-described operations. It is preferred, however, that analysis unit 304 be capable of extrapolating such data from more conventional time lapse data taken from stimulation of the extremities based on user-provided information, for example, the vertebral position of stimulating electrodes 114.

In another embodiment, memory 306 may include a patient-specific evoked response model. More specifically, stimulation of various dermatomes or application of electrical energy through implanted stimulating leads (for example, stimulation leads which require revision due to ineffective pain management but remain capable of delivering applied electrical energy) will desirously result in corresponding evoked responses. Prior to or at the time of the procedure, a pattern of evoked potentials may be recorded and evaluated for given input amplitudes, frequencies, pulse widths, or the like. During the subsequent implantation and positioning of stimulating electrodes 114, evoked potentials may be compared to the previously established evoked potential models at similar amplitudes, frequencies, pulse widths, or the like. An evoked potential model may include not only the measured data but interpolations between specific measured points to provide an effective means to assess applied stimulation between evaluated lateral positions.

While differing embodiments have been described which allow for the comparative filtering of input data, any one of the above techniques may be combined with another. Alternatively, all three techniques may be used to redundantly exclude that information which is not helpful or useful to the implanting user.

While detector 110 of FIG. 4 is limited by its output to a particular display of information, detector 110 of FIG. 5 enables a more user-friendly interface. As an example of information which may be conveyed, FIG. 6 illustrates one possible display embodiment which is coupled to detector 110 of FIG. 5. Display 112' includes a real-time display 402 of measured evoked response (information for this display region is provided exclusively via data line 310 [FIG. 5]); relative medial/lateral positioning indicator 404; and binary indicators 406. As may be noted, indicators 404 and 406 appear to convey information counter to that presented by real-time display 402. As is well known, stimulation on one side of the human body evokes activity in the opposite side of the cerebral cortex. Accordingly, real-time display 402 illustrates that which is detected by detection electrodes 116, while indicators 404 and 406 assimilate the detected information into a readily appreciated format. It should be recognized that FIG. 6 illustrates but one example, and one skilled in the art shall understand that output 112 may take any of a variety of forms to communicate to the user the results of the detected evoked response information, including modification of real-time display 402 to present information in a modified left/right format.

In operation, a patient is pre-operatively prepared, which preferably includes the attachment of detection electrodes 116 and administration of a general anesthetic. The sedated patient is then surgically prepared for implantation in accordance with the selected lead type, whether percutaneous or laminotomy. Upon insertion of the selected lead(s) at a predetermined vertebral position, the implanting physician uses either manual control 108*a* to select at least a pair of electrodes on a first lead 114 and define a particular electrical pulse to be delivered via the selected electrodes or selects a predetermined electrode combination and electrical pulse using automated controls 108*b*. Regardless, controller 102, being responsive to controls 108*a* and 108*b*, applies the directed electrical pulse through stimulation lead 114.

Detection electrodes 116 detect an evoked potential generated as a consequence of the applied electrical pulse. The electrical signals representative of the detected activity are passed through evoked response detector 110 in a manner discussed above and are passed through to output 112. For purposes of this example, detector 110 and output 112 are consistent with that illustrated in FIGS. 5 and 6, respectively.

During application of the directed electrical pulse, the implanting physician causes stimulation lead 114 to move in a transverse direction relative to the dorsal column of the sedated patient. The position of stimulation lead 114 is monitored and communicated to display 112'. For bilateral placement, for example, the implanting physician can confirm bilateral placement notices from indicators 404 and 406 by observing substantially balanced waveforms for the left and the right output regions of real-time display 402. Following implantation of one or more required stimulation leads 114, the patient would be taken to recovery and awakened.

Figure 7:
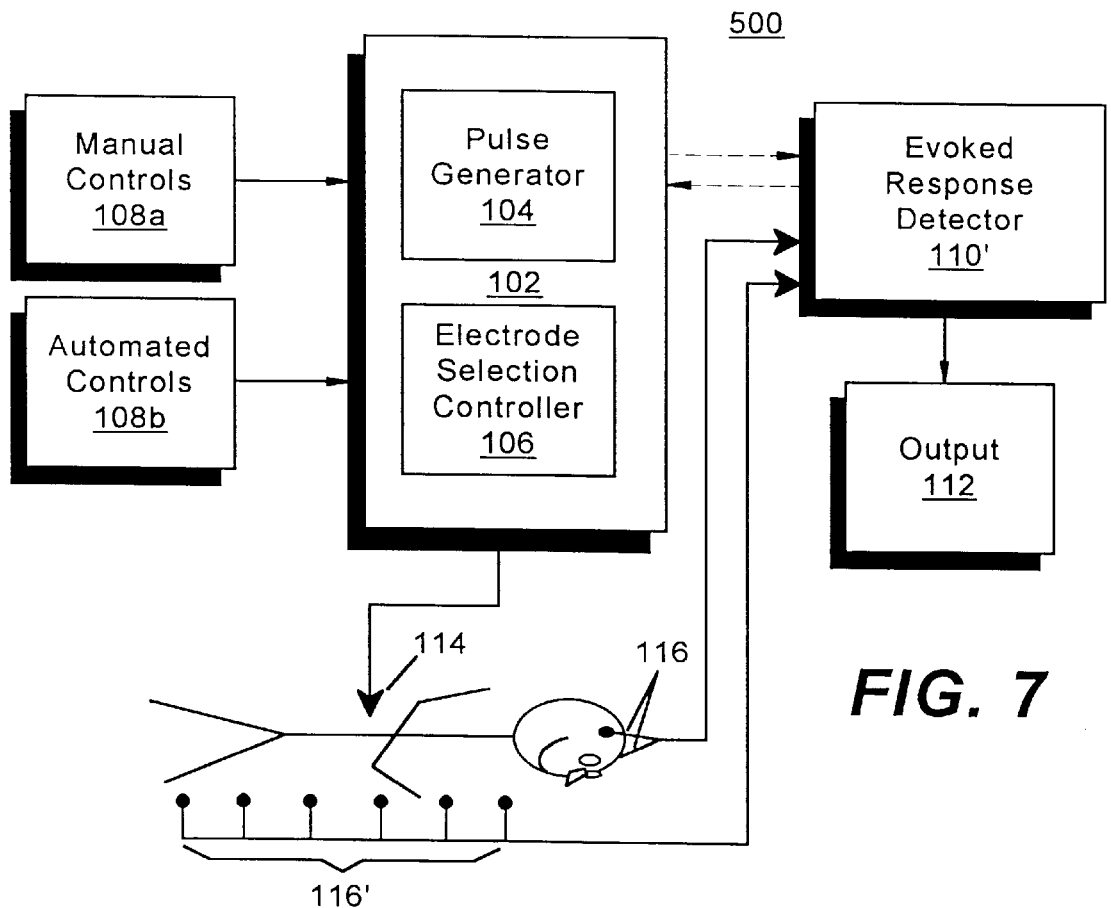
FIG. 7 illustrates another embodiment of a spinal cord placement apparatus in accordance with the present invention.

FIG. 7 illustrates another embodiment of the spinal cord stimulation lead placement device 100 of the present invention. Device 500 enables medial/lateral as well as longitudinal positioning of stimulation leads(s) 114 with respect to the dorsal column of a patient. Device 500 includes input controls 108*a* and 108*b*, stimulation controller 102, and output 112 consistent with that set forth and described above. Device 500 further includes detection electrodes 116' and evoked response detector 110' which is capable of processing input data from both detection electrodes 116 and detection electrodes 116'.

Detection electrodes 116' are conventional, electrically-sensitive electrodes which are capable of detecting galvanic activity from the skin in which the electrodes 116' are attached. The galvanic activity is induced by an electrical pulse applied through stimulation electrodes 114. While electrodes 116' may be placed about the patient's body, detection electrodes 116' are preferably adhered to the skin of a patient at one or more pain-afflicted dermatomes as well as an immediately collateral area about the subject dermatomes. The pain-afflicted dermatomes are carefully identified and isolated through extensive clinical testing and evaluation prior to the implantation procedure.

During the implantation procedure, device 500 functions in a manner consistent with device 100; however, bodily reaction to the applied electrical energy through stimulation electrodes 114 is detectable at both detection electrodes 116 and detection electrodes 116'. In addition to processing information from detection electrodes 116 as described above, detector 110' further processes information from detection electrodes 116' for display and analysis. Specifically, output 112 can communicate which of the detection electrodes 116' detects a response as well as a relative magnitude of any such response. Detector 110' includes filters particularly drawn to filtering signals produced from detection electrodes 116' that may detect spontaneous muscle activity, cardiac activity, and the like, which is otherwise not present for detection electrodes 116.

In application, an implanting physician utilizes the information conveyed from output 112 to first determine a longitudinal position relative to the dorsal column of the patient to effectively address the patient's unique pain pattern, and then subsequently identify a medial/lateral position for each stimulation lead 114. While device 500 has application for both percutaneous leads as well as laminotomy leads, percutaneous leads may be more forgiving and allow the greatest flexibility for longitudinal positioning using device 500.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. An apparatus comprising:
    a signal generating device for generating a stimulation signal;
    at least two stimulation electrodes coupled to the signal generating device and adapted to deliver a stimulation signal from the signal generating device to the spinal nerves of a patient;
    at least two detection electrodes adapted to be positioned at a region of the body of the patient to detect a bodily reaction to the stimulation signal from the signal generating device; and
    a feedback device coupled to the at least two detection electrodes to display information corresponding to at least a position of the at least two stimulation electrodes relative to the dorsal column of the patient.

2. An apparatus in accordance with claim 1, wherein the position relative to the dorsal column of the patient is a medial/lateral position relative to a physiological midline.

3. An apparatus in accordance with claim 1, further comprising one or more additional detection electrodes adapted to be positioned about the body of the patient to detect a bodily reaction to the stimulation signal from the signal generating device, wherein a position of each additional detection electrode corresponds to a bodily region subject to manageable pain.

4. An apparatus in accordance with claim 3, wherein the position relative to the dorsal column of the patient is a longitudinal position along the dorsal column.

5. An apparatus in accordance with claim 3, further comprising an analysis device, coupled between the at least two detection electrodes and the one or more additional detection electrodes and the feedback device, to prepare for display the information corresponding to at least the position of the at least two stimulation electrodes relative to the dorsal column of the patient.

6. An apparatus in accordance with claim 1, further comprising a controller coupled to the signal generating device for selectively defining a stimulation signal.

7. An apparatus in accordance with claim 1, wherein the at least two stimulating electrodes is a plurality of stimulating electrodes, and further comprising a controller coupled to the signal generating device for selecting two or more of the plurality of stimulating electrodes.

8. An apparatus in accordance with claim 1, further comprising an analysis device, coupled between the at least two detection electrodes and the feedback device, to prepare for display the information corresponding to at least the position of the at least two stimulation electrodes relative to the dorsal column of the patient.

9. A spinal cord stimulation lead positioning apparatus having a signal generating device for generating a stimulation signal, the apparatus comprising:
    at least two stimulation electrodes adapted to be positioned approximately adjacent to the dura matter of a patient, wherein the at least two stimulation electrodes are electrically coupled to the signal generating device to deliver a stimulation signal from the signal generating device;
    at least two detection electrodes adapted to be positioned at or about the head of the patient to detect a bodily reaction to the stimulation signal from the signal generating device;
    an analysis unit, coupled to the at least two detection electrodes, to output a signal representative of a detected bodily reaction resulting from the stimulation signal; and
    an output device coupled to the analysis unit and responsive to the signal therefrom to display information corresponding to at least a position of the at least two stimulation electrodes relative to the dorsal column of the patient.

10. An apparatus in accordance with claim 9, wherein the position relative to the dorsal column of the patient is a medial/lateral position relative to a physiological midline.

11. An apparatus in accordance with claim 9, further comprising one or more additional detection electrodes adapted to be positioned about the body of the patient to detect a bodily reaction to the stimulation signal from the signal generating device, wherein a position of each additional detection electrode corresponds to a bodily region subject to manageable pain.

12. An apparatus in accordance with claim 11, wherein the position relative to the dorsal column of the patient is a longitudinal position along the dorsal column.

13. An apparatus in accordance with claim 11, wherein the analysis unit is further coupled to the one or more additional detection electrodes and outputs a signal representative of a bodily reaction detected by the one or more additional detection electrodes.

14. An apparatus in accordance with claim 9, further comprising a controller coupled to the signal generating device for selectively defining a stimulation signal.

15. An apparatus in accordance with claim 9, wherein the at least two stimulating electrodes is a plurality of stimulating electrodes, and further comprising a controller coupled to the signal generating device for selecting two or more of the plurality of stimulating electrodes.

16. A method of positioning dorsal column stimulation electrodes relative to the dorsal column of a patient, the steps comprising:
    providing sensors at or about the head of the patient to detect bodily reaction to stimulation applied to the spinal nerves thereof, wherein the sensors are coupled to a feedback device to display information corresponding to at least a position of the stimulation electrodes relative to the dorsal column of the patient;
    electrically stimulating the spinal nerves of the patient;
    detecting a bodily reaction to the applied electrical stimulation;
    determining a position of the stimulation electrodes relative to the dorsal column of the patient based upon the detected bodily reaction; and
    displaying on the display device information corresponding to the determined position of the stimulation electrodes.

17. A method in accordance with claim 16, further comprising the step of rendering the patient unconscious prior to the step of electrically stimulating the spinal nerves of the patient.

18. A method in accordance with claim 16, wherein the position relative to the dorsal column is a position relative to a physiological midline.

19. A method in accordance with claim 16, further comprising the step of providing sensors about the body of the patient to detect a bodily reaction to the stimulation signal from the signal generating device, wherein a position of each additional detection electrode corresponds to a bodily region subject to manageable pain.

20. A method in accordance with claim 19, wherein the position relative to the dorsal column is a longitudinal position along the dorsal column.

* * * * *